United States Patent [19]

Castaigne

[11] 4,051,141

[45] Sept. 27, 1977

[54] THIENO[3,2-C]PYRIDINE DERIVATIVES

[75] Inventor: Albert Rene Joseph Castaigne, Toulouse, France

[73] Assignee: Centre d'Etudes pour l'Industrie pharmaceutique, Toulouse, France

[21] Appl. No.: 660,248

[22] Filed: Feb. 20, 1976

Related U.S. Application Data

[62] Division of Ser. No. 435,036, Jan. 21, 1974, abandoned.

[30] Foreign Application Priority Data

Feb. 1, 1973 France .................................. 73.03503

[51] Int. Cl.² ............................................ C07D 513/04
[52] U.S. Cl. ............................ 260/294.8 C; 424/256
[58] Field of Search .................... 260/294.8 C, 297 B

[56] References Cited

PUBLICATIONS

Descamps et al., Chem. Abstracts. vol. 59, (2), pp. 1605–1607 July 22, 1963.

*Primary Examiner*—Alan L. Rotman
*Attorney, Agent, or Firm*—Young & Thompson

[57] ABSTRACT

Thieno[3,2-c]pyridine derivatives having the formula:

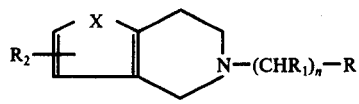

in which X is S; R is a phenyl or benzoyl radical optionally substituted with 1–3 halogen atoms or lower alkyl, lower alkoxy, hydroxy or nitro; $R_1$ is hydrogen, halogen, hydroxy or lower alkyl; $R_2$ is hydrogen or halogen and $n$ is 1 or 2, and in which the symbols $R_1$ may be different in each $CHR_1$ when $n$ is 2; and their pharmaceutically acceptable acid addition salts.

Said derivatives are therapeutically useful for their antiinflammatory, vasodilatator and blood plate aggregation inhibitor action.

6 Claims, No Drawings

THIENO[3,2-c]PYRIDINE DERIVATIVES

This is a division of application Ser. No. 435,036, filed Jan. 21, 1974, now abandoned.

This invention relates to new thieno[3,2-c]pyridine derivatives.

The new compounds of this invention have the following general formula:

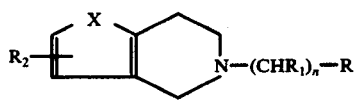
(I)

in which x represents sulfur; R represents a phenyl or benzoyl radical optionally substituted with 1 to 3 halogen atoms or alkyl having 1-6 carbon atoms, alkoxy having 1-6 hydroxy or carbon atoms, nitro; $R_1$ represents hydrogen, halogen or hydroxy or alkyl having 1-6 carbon atoms; $R_2$ is hydrogen or halogen and $n$ is 1 or 2, and in which the symbols $R_1$ may have different meanings in each radical $CHR_1$ when $n$ is 2.

The invention includes also the pharmaceutically acceptable acid addition salts with inorganic or organic acids.

A process for the preparation of compounds of the formula (I) comprises condensing a compound of the formula:

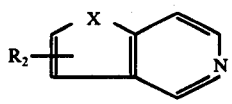
(II)

in which X and $R_2$ have the above meanings, with a halide of the formula

Z—(CHR$_1$)$_n$—R (III)

in which Z represents a halogen atom and R, $R_1$ and $n$ have the aforesaid meanings, to give a pyridinium salt having the formula:

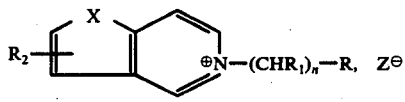
(IV)

and subsequently hydrogenating the pyridinium salt to give the derivative of the formula (I).

The resulting derivatives of the formula (I) may be isolated in free form or as salts.

The condensation reaction is preferably conducted within a medium comprising an inert solvent, such as acetonitrile, for example.

A reducing derivative such as an alkali metal borohydride, e.g., sodium borohydride, will be advantageously used as hydrogenating agent. Said reduction is typically effected at room temperature.

The starting thieno[3,2-c]pyridines having the formula (II) are known compounds which have been described in the literature.

Purification of the products obtained by the process of this invention is preferably effected by extraction with an organic solvent such as ether after addition of a base (such as ammonia), evaporation of the solvent and workup of the residue with an acid (such as HCl) which causes precipitation as crystals which are recrystallised from ethanol, after filtration.

The salts of the compounds of the formula (I) are prepared by methods well known by those expert in the art.

The pyridinium derivatives of the formula (IV) are also new compounds having in particular an antiarrythmic activity and, as such, constitute a feature of the present invention.

The following non-limiting examples are given to illustrate the preparation of compounds of this invention.

EXAMPLE 1

Preparation of 5-(2-chloro-benzyl)-4,5,6,7-tetrahydrothieno[3,2-c]pyridine, as the hydrochloride (derivative 1)

A solution of thieno[3,2-c]pyridine (13.5 g; 0.1 mole) and 2-chloro-benzyl chloride (17.7 g) in acetonitrile (150 ml) is boiled during four hours.

After evaporation of the solvent, the solid residue consists of 5-(2-chloro-benzyl)-thieno[3,2-c]pyridinium chloride which melts at 166° C (derivative n° 30). Said compound is taken up into a solution comprising ethanol (300 ml) and water (100 ml). Sodium borohydride (NaBH$_4$) (20 g) is added portionwise to the solution maintained at room temperature. The reaction medium is maintained under constant stirring during 12 hours and is then evaporated. The residue is taken up into water and made acidic with concentrated hydrochloric acid to destroy the excess reducing agent. The mixture is then made alkaline with ammonia and extracted with ether. The ether solution is washed with water, dried and evaporated. The oily residue is dissolved in isopropanol (50 ml) and hydrochloric acid in ethanol solution is then added thereto.

After filtration and recrystallisation from ethanol, there are obtained 5-(2-chloro-benzyl)-4,5,6,7-tetrahydro-thieno[3,2-c]-pyridine hydrochloride crystals (yield: 60%) having a melting point (Koefler block) of 190° C.

EXAMPLE 2

Preparation of 5-(4-methoxy-benzyl)-4,5,6,7-tetrahydrothieno[3,2-c]pyridine, as the hydrochloride (derivative 2)

Reacting thieno[3,2-c]pyridine (13.5 g; 0.1 mole) with 4-methoxy-benzyl chloride (17.2 g; 0.11 mole) according to the procedure described in Example 1 gives, in a yield of 71%, hydrochloride crystals having a melting point (Koefler block) of 214°-216° C.

EXAMPLE 3

Preparation of 5-(3,4,5-trimethoxy-benzyl)-4,5,6,7-tetrahydro-thieno[3,2-c]pyridine, as the hydrochloride (derivative 3)

Reacting thieno[3,2-c]pyridine (13.5 g; 0.1 mole) with 3,4,5-trimethoxy-benzyl chloride (23.8 g; 0.11 mole), according to the procedure described in Example 1, gives hydrochloride crystals (yield: 79%) having a melting point (Koefler block) of 200°-205° C.

EXAMPLE 4

Preparation of 5-(2-hydroxy-2-phenyl-ethyl)-4,5,6,7-tetrahydro-thieno[3,2-c]pyridine, as the hydrochloride (derivative 4)

Reacting thieno[3,2-c]pyridine (13.5 g) with phenacyl bromide (19.9 g), according to the procedure described in Example 1 (the amount of sodium borohydride is sufficient to hydrogenate both the pyridine ring and the —CO— grouping of phenacyl bromide to convert same to —CHOH—), gives hydrochloride crystals (yield: 61%) having a melting point (Koefler block) of 164°–166° C.

Using analogous procedures, the following compounds were prepared:

derivative 5: 5-parachlorobenzyl-4,5,6,7-tetrahydro-thieno-[3,2-c]pyridine hydrochloride (m.p. = 240° C);

derivative 6: 5-(3,5-dimethoxy-benzyl)-4,5,6,7-tetrahydro-thieno[3,2-c]pyridine hydrochloride (m.p. 195° C);

derivative 7: 5-(3-methoxy-benzyl)-4,5,6,7-thieno[3,2-c]pyridine hydrochloride (m.p. 200° C);

derivative 8: 5-(2-fluoro-benzyl)-4,5,6,7-tetrahydro-thieno[3,2-c]pyridine maleate (m.p. 197°–198° C);

derivative 9: 5-(3,4-dichloro-benzyl)-4,5,6,7-tetrahydro-thieno[3,2-c]pyridine hydrochloride (m.p. 210° C);

derivative 10: 5-(2-phenyl-ethyl)-4,5,6,7-tetrahydro-thieno[3,2-c]pyridine hydrochloride (m.p. 226° C);

derivative 11: 5-[(1-methyl-2-hydroxy-2-phenyl)ethyl]-4,5,6,7-tetrahydro-thieno[3,2-c]pyridine hydrochloride (m.p. 230° C);

derivative 12: 5-(2-methyl-benzyl)-4,5,6,7-tetrahydro-thieno[3,2-c]pyridine hydrochloride (m.p. 208-210° C)

derivative 13: 5-(3-methyl-benzyl)-4,5,6,7-tetrahydro-thieno[3,2-c]pyridine hydrochloride (m.p. 215° C);

derivative 14: 5-(4-methyl-benzyl)-4,5,6,7-tetrahydro-thieno[3,2-c]pyridine hydrochloride (m.p. 260° C);

derivative 15: 5-(4-fluoro-benzyl)-4,5,6,7-tetrahydro-thieno[3,2-c]pyridine hydrochloride, (m.p. 215° C);

derivative 16: 5-(2,6-dichloro-benzyl)-4,5,6,7-tetrahydro-thieno[3,2-c]pyridine hydrochloride (m.p. 200° C);

derivative 17: 5-(2-nitro-benzyl)-4,5,6,7-tetrahydro-thieno[3,2-c]pyridine hydrochloride (m.p. 180° C);

derivative 18: 5-(4-hydroxy-benzyl)-4,5,6,7-tetrahydro-thieno[3,2-c]pyridine hydrochloride (m.p. 240° C);

derivative 19 : 5-[(2-parahydroxyphenyl-2-hydroxy)ethyl]-4,5,6,7-tetrahydro-thieno[3,2-c]-pyridine hydrochloride (m.p. 216° –218° C);

derivative 20 : 5-[(2-paramethoxyphenyl-2-hydroxy)-ethyl]-4,5,6,7-tetrahydro-thieno[3,2-c]pyridine hydrochloride (m.p. 206°–208° C);

derivative 21 : 5-[(2-parachlorophenyl-2-hydroxy)-ethyl]-4,5,6,7-tetrahydro-thieno[3,2-c]pyridine hydrochloride (m.p. 194°–196° C);

derivative 22 : 5-[(2-hydroxy-2-orthomethoxyphenyl)-ethyl]-4,5,6,7-tetrahydro-thieno[3,2-c]pyridine hydrochloride (m.p. 224° C);

derivative 23 : 5-[(2-hydroxy-2-metamethoxyphenyl)-ethyl]-4,5,6,7-tetrahydroxy-thieno[3,2-c]pyridine hydrochloride (m.p. 170° C).

EXAMPLE 5

Synthesis of 5-phenacyl-thieno[3,2-c]pyridinium bromide (derivative No. 24)

A mixture of thieno[3,2-c]pyridine (13.5 g; 0.10 mole) and phenacyl bromide (19.9 g) (0.10 mole) in acetone (200 ml) is stirred during two hours at room temperature.

The resulting white precipitate is filtered, washed with acetone and dried, to give 29.7 g of crude product in a yield of 89%.

Recrystallisation of the material from water (50 ml) and drying gives 26.6 g (recrystallisation yield: 89.5%) highly hygroscopic white crystals having a melting point (Koefler block) of 206°–207° C.

EXAMPLE 6

Synthesis of 5-(O-Methoxy-Phenacyl)-Thieno[3,2-c]Pyridinium bromide (derivative No. 25)

Reaction of thieno[3,2-c]pyridine (13.5 g) with orthomethoxy-phenacyl bromide (21.3 g) according to the procedure of Example 1 gives white crystals (27.34 g) having a melting point (Koefler block) of 258° –260° C.

EXAMPLE 7

Synthesis of 2-chloro-5-phenacyl-thieno[3,2-c]pyridinium bromide (derivative No. 26)

Reaction of 2-chloro-thieno[3,2-c]pyridine (17 g) with phenacyl bromide (20 g) according to the procedure of Example 1 gives white crystals (29.60 g) having a melting point (Koefler block) of 239° C.

EXAMPLE 8

Synthesis of N-parachloro-phenacyl-thieno[3,2-c]pyridinium bromide (derivative No. 27)

Reaction of thieno[3,2-c]pyridine (13.5 g) with parachlorophenacyl bromide (22.5 g) according to the procedure of Example 1 gives white crystals (25.80 g) having a melting point (Koefler block) of 208°–210° C.

Using analogous procedures, the following derivatives are obtained:

derivative No. 28: 5-(3,4-dihydroxy-phenacyl)-thieno[3,2-c]-pyridinium chloride (yellowish crystals, m.p. greater than 260° C);

derivative No. 29: 5-para-fluoro-phenacyl-thieno[3,2-c]pyridinium chloride (white crystals, m.p. 166° C);

derivative No. 30: N-(para-hydroxy-phenacyl)-thieno[3,2-c]pyridinium chloride (brown powder, m.p. 260° C);

derivative No. 31: N-(para-methoxy-phenacyl)-thieno[3,2-c]pyridinium bromide (yellowish-white crystals, m.p. greater than 260° C);

derivative No. 32: N-(meta-methoxy-phenacyl)-thieno[3,2-c]pyridinium bromide (yellowish powder; m.p. 240° C).

The corresponding pyridinium derivatives of the formula (I) are prepared from derivatives 24-32 using the general procedure of Example 1.

The results of toxicological and pharmacological tests reported below demonstrate the useful activities of the derivatives of the formula (I), particularly their anti-inflammatory activity, their vaso-dilatator activity and their inhibitor activity on blood plate aggregation.

Thus, the invention includes also within its scope a therapeutic composition having in particular an anti-inflammatory action, a vasco-dilatator action and an inhibitor action on blood plate aggregation comprising, as active ingredient, a derivative of the formula (I) or a therapeutically acceptable acid addition salt thereof, together with a therapeutically acceptable carrier.

I. TOXICOLOGICAL INVESTIGATION

Said investigation demonstrated the good tolerance of the derivatives of the formula (I).

For indicative purposes, the $LD_{50}/24$ hrs/kg body weight, in mice, calculated according to the method of Miller and Tainter, by the intravenous route, is 60 mg for derivative No. 3, and 55 mg for derivative No. 1.

Orally and for all derivatives, the $LD_{50}/24$ hrs/kg body weight is greater than 300 mg.

The tests have shown that throughout the acute, chronic or delayed toxicity tests, the derivatives of the formula (I) have caused no local or systemic reaction and no changes in the regularly effected biological control tests.

II. PHARMACOLOGICAL INVESTIGATION

1. Anti-inflammatory Action

Said action was investigated according to two methods.

a. Localised Carrageenin-induced Edema Method

A 1% carrageenin solution (1 ml) is injected in the metatarsal flexor muscles of the right hind paw of rats at time O.

The animals of the treated lots are additionally administered orally 100 mg/kg of the test derivative, respectively one hour prior to and then simultaneously with the phlogogenic agent, and then one hour and 2.5 hrs thereafter. The percent anti-inflammatory activity with respect to the reference lot, as a function of time, is determined by measurements effected with a Roch micrometer at times O, one hour, two hours, three hours and five hours after carrageenin administration. The results show that with derivative No. 5, for example, the percentage is and 45% after one hour, 51% after two hours, 52% after three hours and 55% after five hours.

b. Ovalbumin-induced Systemic Edema Method

Rats are administered a simultaneous intraperitoneal injection of 1 ml ovalbumin and 0.5 ml of a 1 aqueous Evans Blue solution. The animals of the treated lot are additionally administered orally 100 mg of the test derivative, one hour prior to ovalbumin administration and simultaneously with said ovalbumin administration. The intensity of the phenomenon thus induced is scored according to a scale from 1 to 5, according to the progress of the inflammatory syndrome. Thus are determined the mean intensity of the edema and the percent decrease of the edema reaction with respect to the control lot. Said percentage, for derivative No. 5, for example, is 62% after two hours and 70% after three hours.

2. Inhibitor Action on Blood Plate Aggregation

The normally cloudy blood plate rich serum of rats is made clear by addition of adenosine diphosphate which induces aggregation of the blood plates. When the same test is effected with serum taken from an animal which has been administered 100 mg/kg of a derivative having an inhibitor effect on blood plate aggregation, there is no aggregation of the blood plates and the serum remains cloudy. Thus, the inhibitor action on blood plate aggregation of the test derivatives may be evaluated by means of a simple spectrophotometric turbidimetric assay.

The tests carried out with lots of five rats (three controls and two treated animals) show that derivatives 1 and 5, for example, protect the test animals against blood plate aggregation in a ratio greater than 95%.

3. Peripheral and Cerebral Vasodilatator Action

This investigation, carried out in rabbits, demonstrated a marked vasodilatator action of the derivatives of the formula (I).

Indeed, administration (perfusion) to the test animals of a solution containing 10 mg/ml per minute, during twenty minutes, produces a substantial vasodilatation of the cerebral blood vessels. Indeed, the rheographic investigation demonstrated a marked increase of the cerebral rate of flow associated with a decrease of the peripheral vascular resistance.

It is apparent from the toxicological and pharmacological investigations reported above that the compounds of the formula (I) are endowed with a good tolerance and that they possess an anti-inflammatory activity, a vasodilatator activity and an inhibitor activity on blood plate aggregation.

The composition of this invention containing, as active ingredient, a derivative of the formula (I), may be formulated for oral administration as tablets, coated tablets, capsules, drops or syrups. It may also be formulated as suppositories for rectal administration and as injectable solutions for parenteral administration.

Each unit dose contains advantageously from 0.025 g to 0.500 g active ingredient, the daily dosage regimen varying within the range from 0.025 g to 1 g active ingredient.

Non limiting examples of pharmaceutical formulations of the composition of this invention are given below.

| EXAMPLE 9 - Tablets | | |
|---|---|---|
| Derivative n°3 | | 0.100 g |
| Talc | | 0.003 g |
| Levilite | | 0.010 g |
| Starch | | 0.010 g |
| Glucose | | 0.025 g |
| EXAMPLE 10 - Coated tablets | | |
| CORE | Derivative n°1 | 0.080 g |
| | Magnesium stearate | 0.010 g |
| | Stearic acid | 0.005 g |
| | Corn starch | 0.020 g |
| | Lactose | 0.015 g |
| COATING | Rosin | 0.003 g |
| | Turpentine | 0.001 g |
| | Shellac | 0.002 g |
| | Gelatin | 0.005 g |
| | Talc | 0.010 g |
| | White wax | 0.002 g |
| | Titanium dioxide | 0.001 g |
| | Erythrosine | Traces |
| | Officinal white sugar, sufficient for 1 coated tablet | |
| EXAMPLE 11 - Capsules | | |
| | Derivative n°2 | 0.150 g |
| | Magnesium stearate | 0.005 g |
| | Talc | 0.005 g |
| EXAMPLE 12 - Drops | | |
| | Derivative n°5 | 2.5 g |
| | Flavoured excipient, sufficient for | 30 ml |

In view of its anti-inflammatory, vasodilatator and blood plate aggregation inhibitor properties, the above composition is usefully administrable for therapeutic purposes.

In short or extended treatments, it is usefully applicable to inflammatory reactions to decrease edema, hypersecretion and exudation and to prevent the organization of the inflammatory injury. It is applicable in the treatment of post-trauma or post-surgical edema, in plastic surgery, in stomatologic surgery, in the treatment of conditions associated with inflammatory reactions (angina, bronchitis, and the like), in inflammatory or degenerative rheumatism and in acute abarticular conditions.

In addition, in view of its inhibitor effects on blood plate aggregation and of its vasodilatator effects, it has a favourable action in the treatment of disorders of the cerebral and peripheral circulatory system and prevents thrombosis-forming complications of atheroma.

The results of toxicological and pharmacological tests reported below demonstrate the useful, particularly anti-arhythmic, activity of the derivatives of the formula (IV).

I. TOXICOLOGICAL INVESTIGATION

Said investigation demonstrated the low toxicity of the derivatives of the formula (IV).

It concerned the acute toxicity, the subacute toxicity, the chronic toxicity, the tolerance and the teratology of said derivatives.

For indicative purposes, the $LD_{50}/24$ hrs/kg body weight in mice, by the intravenous route, is 19 mg for derivative No. 24, 18 mg for derivative No. 25, 38 mg for derivative No. 26, 17.5 mg for derivative No. 27, 16 mg for derivative No. 29, 25 mg for derivative No. 30, 32 mg for derivative No. 31 and 16 mg for derivative No. 32.

The subacute and chronic toxicity tests together with the tolerance tests carried out in rats and dogs have shown that the derivatives of the formula (IV) were free from any noxious action; indeed, both the biological examinations carried out during the tests and the macroscopic and pathologic study of the animals sacrificed at the end of the experiments failed to disclose any anomaly in the treated animals.

The teratologic investigation was carried out in mice, rats and rabbits. It showed that the derivatives of the formula (IV) were free from any effect on the fecundation and the gestation of the female animals and produced no modification of the morphological appearance of the young born during such experimentation.

II. PHARMACOLOGICAL INVESTIGATION

The derivatives of the formula (IV) possess important anti-arhythmic properties.

The tests carried out in rabbits and dogs, according to the method of Schmitt H. and H. Schmitt [Arch. Int. Pharmacodyn., 1960, 127 (1,2)], have shown that at an oral dosage of 5 mg/kg said derivatives protected completely the test animals against arrhythmia induced by barium chloride administration.

There are no regular or dispersed extrasystole bursts in the protected animals.

The same inhibition is also found with respect to other arrhythmia-producing agents such as calcium chloride, K-strophantine, aconitine, isoprenaline, adrenaline and ouabaine.

The anti-arhythmic properties of the compounds of the formula (IV) were also investigated by a different method. Rhythm disorders were produced in dogs by ligation of a coronary artery.

It was shown that administration of a derivative of the formula (IV) was capable of restoring the sinus rhythm and of improving the perturbed electric activity of the heart by causing a reappearance of a rhythmic ventricular activity.

The toxicological and pharmacological investigations reported above demonstrate the good tolerance of the compounds of the formula (IV) and their outstanding anti-arhythmic action.

Thus, the invention includes also within its scope a therapeutic composition having in particular an anti-arhythmic activity, containing, as active ingredient, a compound of the formula

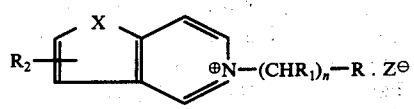

in which X, R, $R_1$, $R_2$, Z and $n$ have the previously defined meanings, and a therapeutically administrable carrier.

This composition containing a derivative of the formula (IV) may be formulated for oral administration as tablets, coated tablets, capsules and drops. It may also be formulated as suppositories for rectal administration and as injectable ampoules for parenteral administration.

Each unit dose contains advantageously from 0.005 to 0.100 g of derivative of the formula (IV) together with therapeutically compatible excipients, the daily dosage regimen varying within a range from 0.005 g to 0.300 g.

Non limiting examples of pharmaceutical formulations of the above composition are given below.

EXAMPLE 15 - Coated tablets

| | | |
|---|---|---|
| Core | Derivative n°24 | 0.025 g |
| | Talc | 0.010 g |
| | Lactose | 0.005 g |
| | Magnesium stearate | 0.005 g |
| | Kaolin | 0.003 g |
| | Starch | 0.005 g |
| | Titanium dioxide | 0.002 g |
| Coating | Starch | 0.010 g |
| | Gum arabic | 0.005 g |
| | White shellac | 0.001 g |
| | White wax | 0.002 g |
| | Sugar syrup sufficient | |
| | | to make 1 coated tablet |

EXAMPLE 16 - Tablets

| | |
|---|---|
| Derivative n°29 | 0.075 g |
| Magnesium hydrocarbonate | 0.020 g |
| Corn starch | 0.010 g |
| Calcium carboxymethyl cellulose | 0.005 g |
| Magnesium stearate | 0.003 g |
| Stearic acid | 0.003 g |
| Talc | 0.003 g |

EXAMPLE 17 - CAPSULES

| | |
|---|---|
| Derivatives n°26 | 0.100 g |
| Wheat starch | 0.025 g |
| Talc | 0.010 g |
| Lactose | 0.010 g |

EXAMPLE 18 - Drops

| | |
|---|---|
| Derivative n°30 | 5.00 g |
| Flavoured excipient, sufficient for | 100 ml |

EXAMPLE 19 - Suppositories

| | |
|---|---|
| Derivative n°24 | 0.025 g |
| Semi-synthetic triglycerides, sufficient to make | 1 suppository |

EXAMPLE 20 - Injectable ampoules

| | |
|---|---|
| Derivatives n°24 | 0.010 g |
| Isotonic solvent, sufficient to make | 3 ml |

In view of their anti-arhythmic action, the derivatives of the formula (IV) are usefully applicable therapeutically whenever it is desired to obtain an anti-arhythmic action either on a healthy heart or on rhythm disorders subsequent to a previous infarction. They exhibit good clinical and biological tolerance, in view of the fact that no signs of blood, renal or liver toxicity could be detected by the routine examinations effected on the patients undergoing treatment.

They are applicable in cardiology in cases of ventricular tachycardia, of ventricular extrasystoles, and in disorders of the cardiac rhythm due to post-digitalization myocardial hyperexcitability. They are also anesthesiologically applicable in the preparation for heart surgery, and for general surgery in old people.

Having now described my invention what I claim as new and desire to secure by Letters Patent is:

1. A compound selected from the derivatives of the formula:

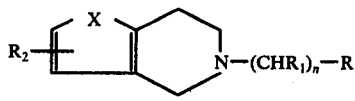

in which X is sulfur; R is selected from the group consisting of phenyl, phenyl substituted with 1 or 2 halogen atoms or alkyl having 1-6 carbon atoms or alkoxy having 1-6 carbon atoms or hydroxy or nitro, benzoyl, and benzoyl substituted with chloro or fluoro or alkyl having 1-6 carbon atoms or alkoxy having 1-6 carbon atoms or 1 or 2 hydroxy groups or nitro; $R_1$ is selected from the group consisting of hydrogen, halogen, hydroxy and alkyl having 1-6 carbon atoms; $R_2$ is selected from hydrogen and halogen and $n$ is 1 or 2, and in which the symbols $R_1$ may have different meanings in each radical —$(CHR_1)$— when $n$ is 2; and the pharmaceutically acceptable acid addition salts thereof.

2. A compound selected from 5-(2-chloro-benzyl)-4,5,6,7-tetrahydro-thieno[3,2-c]pyridine and its pharmaceutically acceptable acid addition salts.

3. A compound selected from 5-(4-methoxybenzyl)-4,5,6,7-tetrahydro-thieno[3,2-c]pyridine and its pharmaceutically acceptable acid addition salts.

4. A compound selected from 5-(3,4,5-trimethoxybenzyl)-4,5,6,7-tetrahydro-thieno[3,2-c]pyridine and its pharmaceutically acceptable acid addition salts.

5. A compound selected from 5-parachlorobenzyl-4,5,6,7-tetrahydro-thieno[3,2-c]pyridine and its pharmaceutically acceptable acid addition salts.

6. A compound selected from 5-(2-fluoro-benzyl)-4,5,6,7-tetrahydro-thieno[3,2-c]pyridine and its pharmaceutically acceptable acid addition salts.

* * * * *

UNITED STATES PATENT AND TRADEMARK OFFICE

CERTIFICATE EXTENDING PATENT TERM
UNDER 35 U.S.C. § 156

PATENT NO.:      4,051,141

DATED:           September 27, 1977

INVENTOR:        Albert Rene Joseph Castaigne

PATENT OWNER:    Sanofi

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks